United States Patent [19]

Rackur et al.

[11] 4,302,468

[45] Nov. 24, 1981

[54] 4-ARYL-5,6,7,8-TETRAHY-DROPYRAZOLO(3,4-B)-(1,5)DIAZEPINE-1H,4H-5,7-DIONES AND MEDICAMENTS CONTAINING SAME

[75] Inventors: Gerhard Rackur, Kelkheim; Irmgard Hoffmann, Bad Soden am Taunus, both of Fed. Rep. of Germany

[73] Assignee: Hoechst Aktiengesellschaft, Frankfurt am Main, Fed. Rep. of Germany

[21] Appl. No.: 177,411

[22] Filed: Aug. 12, 1980

[30] Foreign Application Priority Data

Aug. 14, 1979 [DE] Fed. Rep. of Germany ....... 2932835

[51] Int. Cl.³ .................... A61K 31/55; C07D 487/04; A61K 31/415
[52] U.S. Cl. .................. 424/273 B; 260/239.3 B; 260/159; 548/376; 548/375
[58] Field of Search .............. 260/239.3 B; 424/273 B

[56] References Cited

U.S. PATENT DOCUMENTS 3,558,605  1/1971  De Wald et al. ............ 260/239.3 B Primary Examiner—Robert T. Bond
Attorney, Agent, or Firm—Curtis, Morris & Safford

[57] ABSTRACT

Compound of the general formula

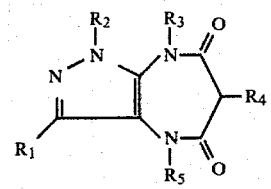

in which $R_1$ and $R_2$ are identical or different and represent hydrogen atoms or alkyl groups with 1-6 C atoms, it also being possible for one of the radicals $R_1$ and $R_2$ to be, in each case, a benzyl, trifluoromethyl or phenyl group, $R_3$ denotes a hydrogen atom, an alkyl group which has 1-6 C atoms and is optionally substituted by an aryl group, an alkoxy group with 1-6 C atoms, a trifluoromethyl group, a dialkylamino group with 2-12 C atoms or a cycloalkyl group with 3-6 C atoms, an alkenyl or alkynyl group with 2-6 C atoms, a cycloalkyl group with 3-6 C atoms or a carbalkoxy group with 2-6 C atoms, $R_4$ is a hydrogen atom and $R_5$ can be a phenyl group, a phenyl group which is monosubstituted or disubstituted by methyl Cl, Br, F, nitro, cyano and or trifluoromethyl or a pyridyl group and medicaments containing same.

4 Claims, No Drawings

4-ARYL-5,6,7,8-TETRAHYDROPYRAZOLO(3,4-B)-(1,5)DIAZEPINE-1H,4H-5,7-DIONES AND MEDICAMENTS CONTAINING SAME

The invention relates to 4-aryl-5,6,7,8-tetrahydropyrazolo(3,4-b)(1,5)diazepine-1H,4H-5,7-diones of the general formula

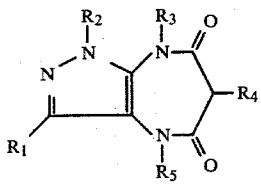

in which $R_1$ and $R_2$ are indentical or different and represent hydrogen atoms or alkyl groups with 1–6 C atoms, it also being possible for one of the radicals $R_1$ and $R_2$ to be, in each case, a benzyl, trifluoromethyl or phenyl group, $R_3$ denotes a hydrogen atom, an alkyl group which has 1–6 C atoms and is optionally substituted by an aryl group, an alkoxy group with 1–6 C atoms, a trifluoromethyl group, a dialkylamino group with 2–12 C atoms or a cycloalkyl group with 3–6 C atoms, an alkenyl or alkynyl group with 2–6 C atoms, a cycloalkyl group with 3–6 C atoms or a carbalkoxy group with 2–6 C atoms, $R_4$ is a hydrogen atom and $R_5$ can be a phenyl group, a phenyl group which is monosubstituted or disubstituted by methyl Cl, Br, F, nitro, cyano and or trifluoromethyl or a pyridyl group.

The invention relates, in particular, to compounds of the formula I in which $R_1$ and $R_2$ are identical or different and denote hydrogen, methyl, ethyl, iso-propyl, or n-butyl, and $R_2$ in some cases can also advantageously be a phenyl or benzyl radical.

The radical $R_3$ can be, in particular, a hydrogen atom, a methyl, ethyl, benzyl, methoxy-, dimethoxy- or trimethoxy-benzyl, propenyl, propynyl or cyclopropyl-methyl group or a methoxymethylene or ethoxymethylene grouping.

$R_5$ can be, in particular, a 2-Cl-phenyl, 3-Cl-phenyl, 4-Cl-phenyl or 2,4-dichlorophenyl group or a corresponding fluorine derivative.

Those compounds of the formula I in which $R_2$ denotes methyl, ethyl or phenyl, $R_1$ is a methyl radical, $R_3$ is hydrogen, methyl, ethyl, cyclopropylmethyl or propynyl, $R_4$ denotes hydrogen and $R_5$ is a phenyl radical or a 2- or 3-chloro- or -fluoro-phenyl radical have particularly favorable properties.

The following compounds can be prepared according to the invention: 1-methyl-4-phenyl-5,6,7,8-tetrahydropyrazolo(3,4-b)(1,5)diazepine-1H,4H-5,7-dione, 1,8-dimethyl-4-phenyl-5,6,7,8-tetrahydropyrazolo(3,4-b)(1,5)-diazepine-1H,4H-5,7-dione, 8-ethyl-1-methyl-4-phenyl-5,6,7,8-tetrahydropyrazolo(3,4-b)(1,5)diazepine-1H,4H-5,7-dione, 8-allyl-1-methyl-4-phenyl-5,6,7,8-tetrahydropyrazolo(3,4-b)(1,5)-diazepine-1H,4H-5,7-dione, 1-methyl-8-(2-propynyl)-4-phenyl-5,6,7,8-tetrahydro(3,4-b)(1,5)-diazepine-1H,4H-5,7-dione, 8-cyclopropylmethyl-1-methyl-4-phenyl-5,6,7,8-tetrahydropyrazolo(3,4-b)(1,5)diazepine-1H,4H-5,7-dione, 1-methyl-8-(2-dimethylaminoethyl)-4-phenyl-5,6,7,8-tetrahydropyrazolo(3,4-b)(1,5)diazepine-1H,4H-5,7-dione, 8-(2-diethylaminoethyl)-1-methyl-4-phenyl-5,6,7,8-tetrahydropyrazolo(3,4-b)(1,5)diazepine-1H,4H-5,7-dione, 8-(2,2,2-trifluoroethyl)-1-methyl-4-phenyl-5,6,7,8-tetrahydropyrazolo(3,4-b)(1,5)diazepine-1H,4H-5,7-dione, 1-methyl-8-(2-methylsulfonylethyl)-4-phenyl-5,6,7,8-tetrahydropyrazolo(3,4-b)(1,5)diazepine-1H,4H-5,7-dione, 1,3-dimethyl-8-ethyl-4-phenyl-5,6,7,8-tetrahydropyrazolo(3,4-b)(1,5)diazepine-1H,4H-5,7-dione, 8-allyl-1,3-dimethyl-4-phenyl-5,6,7,8-tetrahydropyrazolo-(3,4-b)(1,5)diazepine-1H,4H-5,7-dione, 1,3-dimethyl-8-(2-propynyl)-4-phenyl-5,6,7,8-tetrahydropyrazolo(3,4-b)(1,5)-diazepine-1H,4H-5,7-dione, 1,3-dimethyl-8-(dimethylaminoethyl)-4-phenyl-5,6,7,8-tetrahydropyrazolo(3,4-b)(1,5)-diazepine-1H,4H-5,7-dione, 8-(2-diethylaminoethyl)-1,3-dimethyl-4-phenyl-5,6,7,8-tetrahydropyrazolo(3,4-b)(1,5)diazepine-1H,4H-5,7-dione, 1,3-dimethyl-8-(2,2,2-trifluoroethyl)-4-phenyl-5,6,7,8-tetrahydropyrazolo(3,4-b)(1,5)diazepine-1H,4H-5,7-dione, 1,3-dimethyl-8-(2-methylsulfonylethyl)-4-phenyl-5,6,7,8-tetrahydropyrazolo(3,4-b)(1,5)diazepine-1H,4H-5,7-dione, 1,8-diethyl-3-methyl-4-phenyl-5,6,7,8-tetrahydropyrazolo(3,4-b)(1,5)diazepine-1H,4H-5,7-dione, 8-allyl-1-ethyl-3-methyl-4-phenyl-5,6,7,8-tetrahydropyrazolo(3,4-b)(1,5)diazepine-1H,4H-5,7-dione, 1-ethyl-3-methyl-8-(2-propynyl)-4-phenyl-5,6,7,8-tetrahydropyrazolo(3,4-b)(1,5)diazepine-1H,4H-5,7-dione, 8-cyclopropylmethyl-1-ethyl-3-methyl-4-phenyl-5,6,7,8-tetrahydropyrazolo(3,4-b)(1,5)diazepine-1H,4H-5,7-dione, 1-ethyl-3-methyl-8-(2-dimethylaminoethyl)-4-phenyl-5,6,7,8-tetrahydropyrazolo(3,4-b)(1,5)diazepine-1H,4H-5,7-dione, 1-ethyl-8-(2-diethylaminoethyl)-3-methyl-4-phenyl-5,6,7,8-tetrahydropyrazolo(3,4-b)(1,5)-diazepine-1H,4H-5,7-dione, 1-ethyl-8-(2,2,2-trifluoroethyl)-3-methyl-4-phenyl-5,6,7,8-tetrahydropyrazolo-(3,4-b)(1,5)diazepine-1H,4H-5,7-dione, 1-ethyl-3-methyl-8-(2-methylsulfonylethyl)-4-phenyl-5,6,7,8-tetrahydropyrazolo(3,4-b)(1,5)diazepine-1H,4H-5,7-dione, 3-methyl-8-ethyl-1,4-diphenyl-5,6,7,8-tetrahydropyrazolo(3,4-b)(1,5)diazepine-1H,4H-5,7-dione, 8-allyl-3-methyl-1,4-diphenyl-5,6,7,8-tetrahydropyrazolo(3,4-b)(1,5)diazepine-1H,4H-5,7-dione, 3-methyl-1,4-diphenyl-8-(2-propynyl)5,6,7,8-tetrahydropyrazolo(3,4-b)(1,5)diazepine-1H,4H-5,7-dione, 8-cyclopropylmethyl-3-methyl-1,4-diphenyl-5,6,7,8-tetrahydropyrazolo(3,4-b)(1,5)diazepine-1H,4H-5,7-dione, 3-methyl-8-(2-dimethylaminoethyl)-1,4-diphenyl-5,6,7,8-tetrahydropyrazolo(3,4-b)(1,5)diazepine-1H,4H-5,7-dione, 8-(2-diethylaminoethyl)-3-methyl-1,4-diphenyl-5,6,7,8-tetrahydropyrazolo(3,4-b)(1,5)diazepine-1H,4H-5,7-dione, 8-(2,2,2-trifluoroethyl)-3-methyl-1,4-diphenyl-5,6,7,8-tetrahydropyrazolo(3,4-b)(1,5)diazepine-1H,4H-5,7-dione, 3-methyl-8-(2-methylsulfonylethyl)-1,4-diphenyl-5,6,7,8-tetrahydropyrazolo(3,4-b)(1,5)diazepine-1H,4H-5,7-dione, 1-benzyl-8-ethyl-3-methyl-4-phenyl-5,6,7,8-tetrahydropyrazolo(3,4-b)(1,5)diazepine-1H,4H-5,7-dione, 1-benzyl-3-methyl-4-phenyl-8-(2-propynyl)-5,6,7,8-tetrahydropyrazolo(3,4-b)(1,5)diazepine-1H,4H-5,7-dione, 8-allyl-1-benzyl-3-methyl-4-phenyl-5,6,7,8-tetrahydropyrazolo(3,4-b)(1,5)diazepine-1H,4H-5,7-dione, 1-benzyl-8-cyclopropylmethyl-3-methyl-4-phenyl-5,6,7,8-tetrahydropyrazolo(3,4-b)(1,5)diazepine-1H,4H-5,7-dione, 1-benzyl-3-methyl-8-(2-dimethylaminoethyl)-4-phenyl-5,6,7,8-tetrahydropyrazolo(3,4-b)(1,5)diazepine-1H,4H-5,7-dione, 1-benzyl-8-(2-diethylaminoethyl)-3-methyl-4-phenyl-5,6,7,8-tetrahydropyrazolo(3,4-b)(1,5)diazepine-1H,4H-5,7-dione, 1-benzyl-8-(2,2,2-trifluoroethyl)-3-methyl-4-phenyl-tetrahydropyrazolo(3,4-b)(1,5)diazepine-1H,4H-5,7-dione, 1-benzyl-3-methyl-8-(2-methylsulfonylethyl)-4-phenyl-5,6,7,8-tetrahydropyrazolo(3,4- b)(1,5)-diazepine-1H,4H-5,7-dione, 1,3,6-tetramethyl-4-phenyl-5,6,7,8-tetrahydropyrazolo(3,4-b)(1,5)diazepine-1H,4H-5,7-dione, 1,3,6-trimethyl-4-phenyl-5,6,7,8-tetrahydropyrazolo(3,4-b)(1,5)diazepine-1H,4H-5,7-dione, 1,3-dimethyl-6-hydroxy-4-phenyl-5,6,7,8-tetrahydropyrazolo-(3,4-b)(1,5)diazepine-1H,4H-5,7-dione, 1,3-dimethyl-6-oxydimethylcarbamoyl-4-phenyl-5,6,7,8-tetrahydropyrazolo(3,4-b)(1,5)diazepine-1H,4H-5,7-dione, 6-hydroxy-1,3,8-trimethyl-4-phenyl-5,6,7,8-tetrahydropyrazolo(3,4-b)(1,5)-diazepine-1H,4H-5,7-dione, 1,3,8-trimethyl-6-oxydimethylcarbamoyl-4-phenyl-5,6,7,8-tetrahydropyrazolo(3,4-b)(1,5)-diazepine-1H,4H-5,7-dione, 6-hydroxy-1-ethyl-4-methyl-4-phenyl-5,6,7,8-tetrahydropyrazolo(3,4-b)(1,5)diazepine-1H,4H-5,7-dione, 1-ethyl-6-hydroxy-3,8-dimethyl-4-phenyl-5,6,7,8-tetrahydropyrazolo(3,4-b)(1,5)diazepine-1H,4H-5,7-dione, 1-ethyl-3-methyl-6-oxydimethylcarbamoyl-4-phenyl-5,6,7,8-tetrahydropyrazolo(3,4-b)(1,5)-diazepine-1H,4H-5,7-dione, 1-ethyl-3,8-dimethyl-6-oxydimethylcarbamoyl-4-phenyl-5,6,7,8-tetrahydropyrazolo(3,4-b)(1,5)-diazepine-1H,4H-5,7-dione, 6-hydroxy-3-methyl-1,4-diphenyl-5,6,7,8-tetrahydropyrazolo(3,4-b)(1,5)diazepine-1H,4H-5,7-dione, 6-hydroxy-3,8-dimethyl-1,4-diphenyl-5,6,7,8-tetrahydropyrazolo(3,4-b)(1,5)diazepine-1H,4H-5,7-dione, 3-methyl-6-oxydimethylcarbamoyl-1,4-diphenyl-5,6,7,8-tetrahydropyrazolo(3,4-b)(1,5)diazepine-1H,4H-5,7-dione, 3,8-dimethyl-6-oxydimethylcarbamoyl-1,4-diphenyl-5,6,7,8-tetrahydropyrazolo(3,4-b)(1,5)diazepine-1H,4H-5,7-dione, 1-benzyl-3,6-dimethyl-4-phenyl-5,6,7,8-tetrahydropyrazolo(3,4-b)(1,5)diazepine-1H,4H-5,7-dione, 1-benzyl-3,6,8-trimethyl-4-phenyl-5,6,7,8-tetrahydropyrazolo(3,4-b)(1,5)diazepine-1H,4H-5,7-dione, 1-benzyl-6-hydroxy-3-methyl-4-phenyl-5,6,7,8-tetrahydropyrazolo-(3,4-b)(1,5)diazepine-1H,4H-5,7-dione, 1-benzyl-6-hydroxy-3,8-dimethyl-4-phenyl-5,6,7,8-tetrahydropyrazolo-(3,4-b)(1,5)diazepine-1H,4H-5,7-dione, 1-benzyl-3-methyl-6-oxydimethylcarbamoyl-4-phenyl-5,6,7,8-tetrahydropyrazolo(3,4-b)(1,5)diazepine-1H,4H-5,7-dione, 1-benzyl-3,8-dimethyl-6-oxydimethylcarbamoyl-4-phenyl-5,6,7,8-tetrahydropyrazolo(3,4-b)(1,5)diazepine-1H,4H-5,7-dione, 1-methyl-4-(2-chlorophenyl)-5,6,7,8-tetrahydropyrazolo-(3,4-b)(1,5)-diazepine-1H,4H-5,7-dione, 1,8-dimethyl-4-(2,4-dichlorophenyl)-5,6,7,8-tetrahydropyrazolo(3,4-b)(1,5)-diazepine-1H,4H-5,7-dione, 1-methyl-8-allyl-4-(2-pyridyl)-5,6,7,8-tetrahydropyrazolo(3,4-b)(1,5)diazepine-1H,4H-5,7-dione, 1-methyl-8-(2-propynyl)-4-(2-trifluoromethylphenyl)-5,6,7,8-tetrahydropyrazolo(3,4-b)(1,5)-diazepine-1H,4H-5,7-dione, 1-methyl-8-cyclopropylmethyl-4-(o-tolyl)-5,6,7,8-tetrahydropyrazolo(3,4-b)(1,5)diazepine-1H,4H-5,7-dione, 1-methyl-8-(2-dimethylaminoethyl)-4-(3-chlorophenyl)-5,6,7,8-tetrahydropyrazolo(3,4-b)(1,5)-diazepine-1H,4H-5,7-dione, 1-methyl-8-(2-diethylaminoethyl)-4-(3,4-dichlorophenyl)-5,6,7,8-tetrahydropyrazolo-(3,4-b)(1,5)diazepine-1H,4H-5,7-dione, 1-methyl-8-(2,2,2-trifluoroethyl)-4-(4-chlorophenyl)-5,6,7,8-tetrahydropyrazolo(3,4-b)(1,5)diazepine-1H,4H-5,7-dione, 1-methyl-8-(2-methylsulfonylethyl)-4-(p-tolyl)-5,6,7,8-tetrahydropyrazolo(3,4-b)(1,5)diazepine-1H,4H-5,7-dione, 1,3-dimethyl-4-(o-tolyl)-5,6,7,8-tetrahydropyrazolo(3,4-b)(1,5)diazepine-1H,4H-5,7-dione, 1,3,8-trimethyl-4-(3-chlorophenyl)-5,6,7,8-tetrahydropyrazolo(3,4-b)(1,5)-diazepine-1H,4H-5,7-dione, 8-allyl-1,3-dimethyl-4-(3,4-dichlorophenyl)-5,6,7,8-tetrahydropyrazolo(3,4-b)(1,5)-diazepine-1H,4H-5,7-dione, 1,3-dimethyl-8-(2-propynyl)-4-(4-chlorophenyl)-5,6,7,8-tetrahydropyrazolo(3,4-b)(1,5)diazepine-1H,4H-5,7-dione, 1,3-dimethyl-8-cyclopropylmethyl-4-(p-tolyl)-5,6,7,8-tetrahydropyrazolo(3,4-b)(1,5)diazepine-1H,4H-5,7-dione, 1,3-dimethyl-8-(2-dimethylaminoethyl)-4-(2-chlorophenyl)-5,6,7,8-tetrahydropyrazolo(3,4-b)(1,5)diazepine-1H,4H-5,7-dione, 1,3-dimethyl-8-(2-diethylaminoethyl)-4-(2,4-dichlorophenyl)-5,6,7,8-tetrahydropyrazolo(3,4-b)(1,5)diazepine-1H,4H-5,7-dione, 1,3-dimethyl-8-(2,2,2-trifluoroethyl)-4-(2-cyanophenyl)-5,6,7,8-tetrahydropyrazolo(3,4-b)(1,5)-diazepine-1H,4H-5,7-dione, 1,3-dimethyl-8-(2-methylsulfonylethyl)-4-(2-trifluoromethylphenyl)-5,6,7,8-tetrahydropyrazolo(3,4-b)(1,5-diazepine-1H,4H-5,7-dione, 1-ethyl-3,8-dimethyl-4-(2-chlorophenyl)-5,6,7,8-tetrahydropyrazolo(3,4-b)(1,5)diazepine-1H,4H-5,7-dione, 8-allyl-1-ethyl-3-methyl-4-(2,4-dichlorophenyl)-5,6,7,8-tetrahydropyrazolo(3,4-b)(1,5)diazepine-1H,4H-5,7-dione, 1-ethyl-3-methyl-8-(2-propynyl)-4-(2-pyridyl)-5,6,7,8-tetrahydropyrazolo(3,4-b)(1,5)diazepine-1H,4H-5,7-dione, 8-cyclopropylmethyl-1-ethyl-3-methyl-4-(2-trifluoromethylphenyl)-5,6,7,8-tetrahydropyrazolo(3,4-b)(1,5)diazepine-1H,4H-5,7-dione, 1-ethyl-3-methyl-8-(2-dimethylaminoethyl)-4-(o-tolyl)-5,6,7,8-tetrahydropyrazolo(3,4-b)(1,5)diazepine-1H,4H-5,7-dione, 1-ethyl-3-methyl-8-(2-methylsulfonylethyl)-4-(4-chlorophenyl)-5,6,7,8-tetrahydropyrazolo(3,4-b)(1,5)diazepine-1H,4H-5,7-dione, 1-phenyl-3,8-dimethyl-4-(m-tolyl)-5,6,7,8-tetrahydropyrazolo(3,4-b)(1,5)diazepine-1H,4H-5,7-dione, 8-allyl-3-methyl-1-phenyl-4-(3,4-dichlorophenyl)-5,6,7,8-tetrahydropyrazolo(3,4-b)(1,5)diazepine-1H,4H-5,7-dione, 3-methyl-1-phenyl-8-(2-propynyl)-4-(3-chlorophenyl)-5,6,7,8-tetrahydropyrazolo(3,4-b)(1,5)diazepine-1H,4H-5,7-dione, 8-cyclopropylmethyl-3-methyl-1-phenyl-4-(2-cyanophenyl)-5,6,7,8-tetrahydropyrazolo(3,4-b)(1,5)diazepine-1H,4H-5,7-dione, 3-methyl-8-(2-dimethylaminoethyl)-1-phenyl-4-(2-pyridyl)-5,6,7,8-tetrahydropyrazolo(3,4-b)(1,5)diazepine-1H,4H-5,7-dione, 8-(2-diethylaminoethyl)-3-methyl-1-phenyl-4-(2-chlorophenyl)-5,6,7,8-tetrahydropyrazolo(3,4-b)(1,5)diazepine-1H,4H-5,7-dione, 8-(2,2,2-trifluoroethyl)-3-methyl-1-phenyl-4-(o-tolyl)-5,6,7,8-tetrahydropyrazolo(3,4-b)(1,5)diazepine-1H,4H-5,7-dione, 3-methyl-1-phenyl-8-(2methylsulfonylethyl)-4-(2,4-dichlorophenyl)-5,6,7,8-tetrahydropyrazolo(3,4-b)(1,5)diazepine-1H,4H-5,7-dione, 1-benzyl-3,8-dimethyl-4-(2-chlorophenyl)-5,6,7,8-tetrahydropyrazolo(3,4-b)(1,5)diazepine-1H,4H-5,7-dione, 8-allyl-1-benzyl-3-methyl-4-(3,4-dichlorophenyl)-5,6,7,8-tetrahydropyrazolo(3,4-b)(1,5)diazepine-1H,4H-5,7-dione, 1-benzyl-3-methyl-8-(2-propynyl)-4-(o-tolyl)-5,6,7,8-tetrahydropyrazolo(3,4-b)(1,5)diazepine-1H,4H-5,7-dione, 1-benzyl-8-cyclopropylmethyl-3-methyl-4-(4-chlorophenyl)-5,6,7,8-tetrahydropyrazolo(3,4-b)(1,5)diazepine-1H,4H-5,7-dione, 1-benzyl-3-methyl-8-(2-dimethylaminoethyl)-4-(3-chlorophenyl)-5,6,7,8-tetrahydropyrazolo(3,4-b)(1,5)diazepine-1H,4H-5,7-dione, 1-benzyl-3-methyl-8-(2-diethylaminoethyl)-4-(2-trifluoromethylphenyl)-5,6,7,8-tetrahydropyrazolo(3,4-b)(1,5)diazepine-1H,4H-5,7-dione, 1-benzyl-3-methyl-8-(2,2,2-trifluoroethyl)-4-(4-chlorophenyl)-5,6,7,8-tetrahydropyrazolo(3,4-b)(1,5)diazepine-1H,4H-5,7-dione, 1-benzyl-3-methyl-8-(2-methylsulfonylethyl)-4-(2-cyanophenyl)-5,6,7,8-tetrahydropyrazolo(3,4-b)(1,5)diazepine-1H,4H-5,7-dione, 1,3,6-trimethyl-4-(2-trifluoromethylphenyl)-5,6,7,8-tetrahydropyrazolo(3,4-b)(1,5)diazepine-1H,4H-5,7-dione, 1,3,6-tetramethyl-4-(o-tolyl)-5,6,7,8-tetrahydropyrazolo(3,4-b)(1,5)diazepine-1H,4H-5,7-dione, 1,3- dimethyl-6-hydroxy-4-(2,4-dichlorophenyl)-5,6,7,8-tetrahydropyrazolo(3,4-b)(1,5)diazepine-1H,4H-5,7-dione, 1,3,8-trimethyl-6-hydroxy-4-(2-pyridyl)-5,6,7,8-tetrahydropyrazolo(3,4-b)(1,5)diazepine-1H,4H-5,7-dione, 1,3-dimethyl-6-oxydimethylcarbamoyl-4-(2-chlorophenyl)-5,6,7,8-tetrahydropyrazolo(3,4-b)(1,5)diazepine-1H,4H-5,7-dione, 1,3,8-trimethyl-6-oxydimethylcarbamoyl-4-(m-tolyl)-5,6,7,8-tetrahydropyrazolo(3,4-b)(1,5)diazepine-1H,4H-5,7-dione, 1-ethyl-3-methyl-6-hydroxy-4-(2,4-dichlorophenyl)-5,6,7,8-tetrahydropyrazolo(3,4-b)(1,5)-diazepine-1H,4H-5,7-dione, 1-ethyl-3,8-dimethyl-6-hydroxy-4-(2-cyanophenyl)-5,6,7,8-tetrahydropyrazolo-(3,4-b)(1,5)diazepine-1H,4H-5,7-dione, 1-ethyl-3-methyl-6-oxydimethylcarbamoyl-4-(2-pyridyl)-5,6,7,8-tetrahydropyrazolo(3,4-b)(1,5)diazepine-1H,4H-5,7-dione, 1-ethyl-3,8-dimethyl-6-oxydimethylcarbamoyl-4-(3-chlorophenyl)-5,6,7,8-tetrahydropyrazolo(3,4-b)(1,5)diazepine-1H,4H-5,7-dione, 1-ethyl-3,6-dimethyl-4-(4-chlorophenyl)-5,6,7,8-tetrahydropyrazolo(3,4-b)(1,5)diazepine-1H,4H-5,7-dione, 1-ethyl-3,6,8-trimethyl-4-(m-tolyl)-5,6,7,8-tetrahydropyrazolo(3,4-b)(1,5)diazepine-1H,4H-5,7-dione, 3,6-dimethyl-1-phenyl-4-(3,4-dichlorophenyl)-5,6,7,8-tetrahydropyrazolo(3,4-b)(1,5)diazepine-1H,4H-5,7-dione, 3,6,8-trimethyl-1-phenyl-4-(2-trifluoromethylphenyl)-5,6,7,8-tetrahydropyrazolo(3,4-b)(1,5)diazepine-1H,4H-5,7-dione, 3-methyl-1-phenyl-6-hydroxy-4-(2-cyanophenyl)-5,6,7,8-tetrahydropyrazolo(3,4-b)(1,5)diazepine-1H,4H-5,7-dione, 3,8-dimethyl-1-phenyl-6-oxymethylcarbamoyl-4-(2-bromophenyl)-5,6,7,8-tetrahydropyrazolo(3,4-b)(1,5)diazepine-1H,4H-5,7-dione, 3,8-dimethyl-1-phenyl-6-hydroxy-4-(3-bromophenyl)-5,6,7,8-tetrahydropyrazolo(3,4-b)(1,5)diazepine-1H,4H-5,7-dione, 3-methyl-1-phenyl-6-oxydimethyl-carbamoyl-4-(4-bromophenyl)-5,6,7,8-tetrahydropyrazolo(3,4-b)(1,5)diazepine-1H,4H-5,7-dione, 1-benzyl-3,6-dimethyl-4-(2-pyridyl)-5,6,7,8-tetrahydropyrazolo(3,4-b)(1,5)-diazepine-1H,4H-5,7-dione, 1-benzyl-3,6,8-trimethyl-4-(o-tolyl)-5,6,7,8-tetrahydropyrazolo(3,4-b)(1,5)diazepine-1H,4H-5,7-dione, 1-benzyl-6-hydroxy-3-methyl-4-(2-trifluoromethyl)-5,6,7,8-tetrahydropyrazolo(3,4-b)(1,5)diazepine-1H,4H-5,7-dione, 1-benzyl-6-hydroxy-3,8-dimethyl-4-(2,4-dichlorophenyl)-5,6,7,8-tetrahydropyrazolo(3,4-b)(1,5)diazepine-1H,4H-5,7-dione, 1-benzyl-3-methyl-6-oxydimethylcarbamoyl-4-(2-cyanophenyl)-5,6,7,8-tetrahydropyrazolo(3,4-b)(1,5)diazepine-1H,4H-5,7-dione and 1-benzyl-3,8-dimethyl-6-oxydimethylcarbamoyl-4-(3,4-dichlorophenyl)-5,6,7,8-tetrahydropyrazolo(3,4-b)(1,5)diazepine-1H,4H-5,7-dione.

The compounds prepared according to the invention have outstanding pharmacological properties, and in particular they have an anxiolytic action.

The invention also relates to processes for their preparation, to pharmaceutical preparations containing them and to their use as medicaments.

The compounds can be prepared in known manner by (a) cyclizing a compound of the general formula

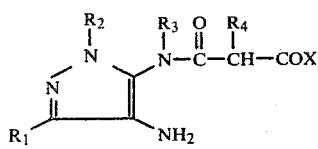

II in which $R_1$, $R_2$, $R_3$ (with the exception of hydrogen) and $R_4$ have the abovementioned meanings and X denotes a hydroxyl group, a mercapto group, a halogen atom, an alkoxy group, an alkylmercapto group, an amino group, an alkylamino group, a dialkylamino group, a benzoyloxy group, an aryloxy group, an acyloxy group or the group $N_3$, to form the seven-membered ring; or (b) subjecting a compound of the general formula

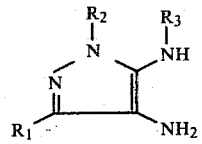

III in which $R_1$, $R_2$ and $R_3$ (with the exception of hydrogen) have the abovementioned meaning, to a condensation reaction with an activated malonic acid derivative, for example a malonic acid dihalide, a malonic acid ester, carbon suboxide or Meldrum's acid, or with malonic acid itself, to form the seven-membered ring; or (c) cyclizing a compound of the general formula

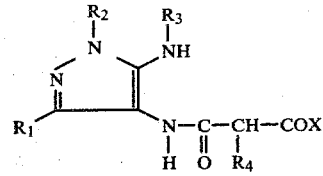

IV in which $R_1$, $R_2$, $R_3$ (with the exception of hydrogen) and $R_4$ have the abovementioned meaning and X can be the groups indicated under (a), by the processes described under (a) to form the seven-membered ring.

Process (a) can be carried out with or without a solvent, by heating the compound to 50°–250° C., a condensation agent customary for such reactions being added if appropriate. Examples of possible solvents are: aliphatic alcohols (methanol and ethanol), dioxan, dimethylformamide, benzene, toluene, glacial acetic acid, polyphosphoric acid, $H_2SO_4$ or aqueous or alcoholic HCl, the last three compounds being condensation agents which can also be used in the solvents mentioned. Other possible condensation agents are: metal alcoholates, in particular alkali metal alcoholates, alkali metal amides, alkali metal hydrides (NaH), strong acids, such as trifluoroacetic acid or p-toluenesulfonic acid, and also dehydrating agents, such as dicyclohexylcarbodiimide and the like. The halogen atoms in process (a) can be, preferably, Cl or Br, or also the halogen-like group $N_3$. If X is an alkoxy group, an alkylmercapto group, an alkylamino group or a dialkylamino group, this group in general has alkyl radicals with 1 to 6 C atoms. If X denotes an acyloxy group, the acyl group is preferably an aliphatic acyl group with 2 to 6 C atoms. An aryloxy group is preferably a phenoxy group.

Process (b) comprises reacting the activated malonic acid derivative using a suitable inert solvent, such as, for example, benzene, toluene, xylene, ether, tetrahydrofuran, dioxan or dimethylformamide, at room temperature or more advantageously at the boiling point of the particular solvent. In some cases, the addition of a tertiary organic base, such as, for example, pyridine, triethylamine and the like, also proves favorable for the progress of the reaction. The reaction with malonic acid is best carried out using strong acids, such as, for example HCl, $H_2SO_4$, trifluoroacetic acid, polyphosphoric acid and the like.

Process (c) comprises carrying out the cyclization to form the seven-membered ring under the same conditions as for process (a).

The compounds of the general formula

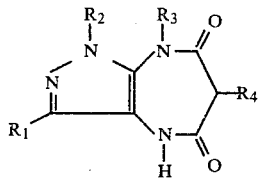

accessible by processes (a) to (c) can then be arylated or hetero-arylated on the nitrogen in the 4-position by a process which was first described by I. Goldberg (Ber. 40, 4541 (1907)) for the preparation of N-acetyldiarylamines. In this process, V is reacted with a compound of the general formula

R$_5$X                  VI in which R$_5$ has the abovementioned meaning and X is a halogen atom, preferably chlorine or bromine.

The arylation is carried out in the presence of copper powder, copper-I salts or copper-II salts or mixtures thereof, either using the aryl halide of the general formula VI in excess or in polar aprotic solvents, such as, for example, dimethylformamide, dimethylsulfoxide or hexamethylphosphoric acid triamide. If solvents are used, the aryl halide is added in an amount which is only slightly more than the equimolar amount. The reaction temperature depends on the particular starting substances employed and is in general between 90° and 180° C. It is necessary to add a suitable organic or inorganic base, for example an alkali metal carbonate, bicarbonate or alcoholate, preferably an alkali metal acetate, in molar amounts or in excess, as a basic catalyst and as a base for bonding the hydrogen halide formed.

Compounds of the formula I in which R$_1$, R$_2$, R$_4$ and R$_5$ have the abovementioned meaning and R$_3$ is a hydrogen atom can be prepared, for example, in the following way: a compound of the general formula I in which R$_1$, R$_2$, R$_4$ and R$_5$ have the abovementioned meaning and R$_3$ is a radical which can be split off when the synthesis has ended is synthesized, as described. Examples of possible radicals R$_3$ are the benzyl radical, which can be split off hydrogenolytically, or the methoxy-, dimethoxy- or trimethoxy-benzyl radical, which can be split off under acid conditions. The catalytic hydrogenation can be carried out, for example, with Pd, Pt or Raney nickel in alcohols, dioxan, tetrahydrofuran or ethyl acetate, at 60°–150° C. and under a hydrogen pressure of 1–150 atmospheres. The splitting off under acid conditions can be carried out in the presence of mineral acid, such as HCl or H$_2$SO$_4$, in organic solvents, for example alcohols, or in the presence of strong organic acids, such as trifluoroacetic acid or toluenesulfonic acid, in organic solvents, such as alcohols, chlorinated hydrocarbons and the like.

Subsequent introduction of the radical R$_4$ by alkylation or acylation is effected by the known methods. For example, compounds of the formula I in which R$_4$ is a hydrogen atom can be converted into a mono-(alkali metal) salt with proton acceptors, such as, for example, sodium hydride, sodium amide, potassium tert.-butylate or finely divided sodium, in an inert solvent and the mono-(alkali metal) salt can then be alkylated or acylated in a manner which is known per se. Examples of possible alkylating agents are esters of the formula RHal, ArSO$_2$OR and SO$_2$(OR)$_2$, in which Hal is a halogen atom (in particular Cl, Br or I) and Ar is an aromatic radical, such as, for example, phenyl or a phenyl radical which is monosubstituted for polysubstituted by lower alkyl radicals. R is in each case one of the groups listed under R$_4$ (with the exception of H). The acylation can be carried out under the same conditions. Examples of possible acylating agents are: ketenes and acid halides, acid anhydrides or acid esters of aliphatic carboxylic acids with 2 to 6 C atoms and of carbonic acid halfester halides with 1 to 6 C atoms.

The starting materials used for processes (a), (b) and (c) can be obtained in the following ways:

(a) a compound of the general formula

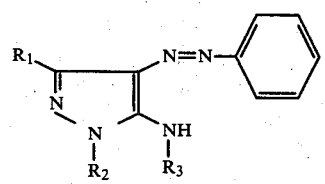

in which R$_1$, R$_2$ and R$_3$ (with the exception of hydrogen) have the abovementioned meaning, is reacted with a compound of the formula

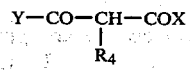

in which R$_4$ and X have the abovementioned meaning and Y denotes a chlorine or bromine atom, an azido group (N$_3$) or an alkoxy or aryloxy group, in an inert solvent, such as dioxan, tetrahydrofuran, chloroform, benzene or toluene, at temperatures between 0° and 200° C., with or without the addition of an acid acceptor, to give a compound of the formula

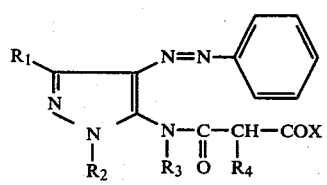

The azo group in this compound is then subjected to reductive splitting, whereupon the amino compound of the formula II is formed. The reductive splitting of the azo group can be effected by catalytic hydrogenation (with Pd, Pt or Raney nickel in alcohols, dioxan or tetrahydrofuran, at 0°–60° C. and under a H$_2$ pressure of 1–50 atmospheres), or by chemical reduction, for example with sodium dithionite in aqueous or alcoholic solution, with SnCl$_2$ in HCl or with zinc in glacial acetic acid or neutral, acid or alkaline aqueous solution.

The starting materials of the formula V are accessible in the manner described by F. A. Amer, A. H. Harhash and M. L. Awad (Z. Naturforsch. 33 b, 660–662 (1978)), or they can be synthesized as follows:

A pyrazolone of the general formula

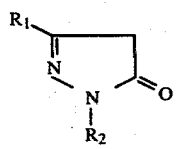

VIII is reacted with benzenediazonium chloride in glacial acetic acid at 0°–5° C. to give the phenylhydrazone of the general formula

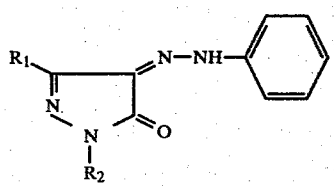

IX which can then be chlorinated in the 5-position in boiling POCl₃ to give the 4-benzene-azo-5-chloropyrazole of the general formula

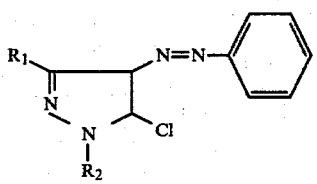

X

The chlorine radical is then replaced by an appropriately substituted amine R₃NH₂, in which R₃ has the above-mentioned meaning, with the exception of hydrogen, at 100°–160° C., with or without a solvent, whereupon the compound of the general formula V is formed.

Compounds of the general formula II can also be obtained in the following way:

A compound of the general formula X

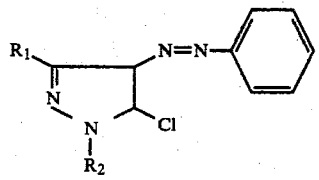

X (for the synthesis, see above) is reacted with a compound of the general formula

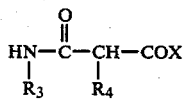

XI in which R₃ (with the exception of hydrogen) and R₄ have the meaning indicated and X can be the radicals indicated, with the exception of halogen, NH₂, alkylamino and azido (N₃), to give a compound of the formula VII. This reaction is in general carried out in an inert solvent, such as, for example, dioxan, tetrahydrofuran or dimethylformamide, with the addition of a proton acceptor, such as NaH, sodium amide or finely divided sodium. The temperatures of the reaction are between 0° and 150° C.

Compounds of the formula II in which X is halogen can be obtained, for example, from compounds of the formula II in which X is OH, by reaction with halogenating agents, such as thionyl chloride or phosphorus pentachloride, at temperatures between 0° and 100° C. in inert solvents, such as benzene, toluene, dioxan or tetrahydrofuran. The carboxylic acids of the formula II (X=OH) can be obtained, for example, from the corresponding ester (X=alkoxy, aryloxy or benzyloxy), by converting these into the acid under mild conditions, for example by hydrogenation (if X=benzyloxy) or by very mild hydrolysis (if X=aryloxy or a branched alkoxy radical, such as tert.-butoxy). Compounds of the formula II in which X is an acyloxy group can also be obtained from the corresponding halides by reaction with the corresponding metal salts in inert solvents, such as acetone, dioxan or ether, at temperatures between −20° and 100° C.

Compounds of the formula II in which X is an azido group can be obtained, for example, from the corresponding halides by reaction with alkali metal azides in inert solvents, such as acetone, dioxan or dimethylsulfoxide, at temperatures between 0° and 100° C., or from esters (X=O-alkyl or O-aryl) by reaction with hydrazine, if appropriate in an inert solvent, such as ethanol, dioxan, or tetrahydrofuran, at 0° to 100° C. and subsequent reaction of the hydrazine with nitrous acid or nitrous gases in inert solvents, such as alcohols, dioxan or dimethylformamide, at temperatures between 0° and 50° C.

Those starting substances of the formula XI which are not known are obtained as follows:

An amine R₃—NH₂, in which R₃ (with the exception of hydrogen) has the abovementioned meaning, is reacted with a compound of the formula VI in which R₄ and X have the abovementioned meanings (with the exception of halogen, NH₂, alkylamino and azido for X) and Y denotes a chlorine or bromine atom, an azido group or an alkoxy or aryloxy group, in an inert solvent, such as dioxan, tetrahydrofuran, chloroform or acetone, or also in an excess of the compound VI, at temperatures between 0° and 200° C. The procedure followed here can be, for example, analogous to that in Chem.Ber. 17, 739 et seq. (1884) or J. Indian Chem.Soc. 37, 591–593 (1960).

(b) In the case of the compound of the general formula V, the azo group is subjected to reductive splitting under the abovementioned conditions to give a compound of the general formula III.

(c) Compounds of the general formula IV are accessible by reacting compounds of the general formula III with compounds of the general formula VI, the amino group in the 4-position of the pyrazole ring reacting selectively. The reaction can be carried out in an inert solvent, such as, for example, benzene, toluene, dioxan, tetrahydrofuran or chloroform, with or without the addition of an acid acceptor and between 0° and 150° C.

The compounds according to the invention are suitable for the production of medicaments. The medicaments can contain one or more of the compounds according to the invention, or also mixtures thereof with other pharmaceutically active substances. The customary pharmaceutical excipients and auxiliaries and galenic processes which are known per se can be used for the production of the medicaments. The medicaments can be applied enterally, parenterally, orally or perlingually. For example, administration can be effected in the form of tablets, capsules, pills, dragees, suppositories, gels, creams, powders, liquids, dusting powders or aerosols. Examples of possible liquids are: oily or aqueous solutions or suspensions, emulsions and injectable aqueous solutions or suspensions.

The compounds according to the invention have outstanding pharmacological properties, and in particular they have an anxiolytic action. Possible indications are thus insomnia, emotional tension and autonomic depression.

The pharmaceutical formulations in general contain between 1 and 10% of the active component(s) according to the invention.

The anxiolytic action is accompanied by a very low level of sedation and good tolerances ($LD_{50}$ is in general >1,200 mg/kg on peroral administration to mice). This is found from investigations in which the influence of the compounds according to the invention on the motor activity, the hexobarbital narcosis and the cardiazol cramp in mice was measured. In addition, the hamster taming test and the Geller anxiolysis test in rats were also used.

The lowest dose which is already effective in the abovementioned experiments is, for example, 5 mg/kg orally, 2.5 mg/kg sublingually and 1 mg/kg intravenously. A general dosage range for the action (animal experiments as above) is, for example: 5 to 50 mg/kg orally, 2.5 to 25 mg/kg sublingually and 1 to 10 mg/kg intravenously.

For example, the recommendation can be 1 to 3 tablets, containing 10 to 100 mg of active substance, 3 times daily or, for example in the case of intravenous injection, one ampoule containing 2 to 4 ml with 0.5 to 5 mg of substance, 1 to 3 times daily. However, the maximum daily dose should not be greater than 200 mg.

In addition the substances have a nootropic effect as could be ascertained by several test methods. In the One-Trial-Dark-Avoidance-Test the substance is 20 to 40 times more effective than the comparative substance Piracetam. The lowest effective dose in this test is 12.5 mg/kg orally, whereas the lowest effective dose of Piracetam is 500 mg/kg orally. A further distinct activity could be observed with respect to the Gamma-Butyrolacton-Antagonism, the Brevatonal-Antagonism in rats and mice. To characterize the nootropic properties of the substance the suffocation test on mice was used, too.

The following examples illustrate the invention.

EXAMPLE 1

1,3,8-Trimethyl-4-phenyl-5,6,7,8-tetrahydropyrazolo(3,4-b)(1,5)diazepine-1H,4H-5,7-dione (a) 4-Amino-1,3-dimethyl-5-methylaminopyrazole 23 g (0.1 mole) of 4-benzene-azo-1,3-dimethyl-5-methylaminopyrazole are hydrogenated in 250 ml of ethanol with 60 g of Raney nickel, at 60° C. and under a hydrogen pressure of 50 atmospheres. When the uptake of hydrogen has ended, the catalyst is filtered off and the reaction solution is evaporated in vacuo. The residue is triturated with ether/petroleum ether and the precipitate is filtered off. The product is sufficiently pure for the subsequent reactions. Melting point: 87° C.

(b) 4-α-Ethoxycarbonylacetylamino-1,3-dimethyl-5-methylaminopyrazole 1.4 g (0.01 mole) of 4-amino-1,3-dimethyl-5-methylaminopyrazole are dissolved in 20 ml of toluene, 1 ml (0.012 mole) of monomethyl malonate chloride is slowly added dropwise, whilst cooling with ice, and the mixture is subsequently stirred at room temperature for one hour. The toluene is stripped off in vacuo, the residue is taken up in chloroform and the mixture is washed with ice-cold $NaHCO_3$ solution and water and dried with $Na_2SO_4$. After evaporating off the solvent, a yellowish oil remains which does not crystallize.

(c) 1,3,8-Trimethyl-5,6,7,8-tetrahydropyrazolo(3,4-b)(1,5)diazepine-1H,4H-5,7-dione 15 ml of a 1 molar sodium methanolate solution are added to 2.4 g (0.01 mole) of 4-α-ethoxycarbonylacetylamino-1,3-dimethyl-5-methyl-aminopyrazole, dissolved in 100 ml of ethanol, and the mixture is stirred at room temperature for 8 hours. It is then neutralized with alcoholic HCl and evaporated in vacuo, the residue is taken up in $CHCl_3$, the mixture is filtered and the filtrate is again evaporated. After adding ether to the residue, the latter becomes crystalline and can be filtered off. It is recrystallized from isopropanol/diisopropyl ether. Melting point: 202° C.

(d) 1,3,8-Trimethyl-4-phenyl-5,6,7,8-tetrahydropyrazolo(3,4-b)(1,5)diazepine-1H,4H-5,7-dione A mixture of 1 g of 1,3,8-trimethyl-5,6,7,8-tetrahydropyrazolo(3,4-b)(1,5)diazepine-1H,4H-5,7-dione, 1 g of potassium acetate and 1.5 g of copper powder in 100 ml of bromobenzene is boiled under reflux, whilst stirring, until the reaction has ended (monitoring by thin layer chromatography, 3–4 hours). The mixture is then allowed to cool to room temperature and is diluted with $CH_2Cl_2$ (200 ml), the inorganic constituents are filtered off, the organic phase is washed with water and dried and the solvent is stripped off in vacuo. Recrystallization of the residue from diisopropyl ether gives the analytically pure product. Melting point: 168° C.

EXAMPLE 2

1-Ethyl-3,8-dimethyl-4-phenyl-5,6,7,8-tetrahydropyrazolo(3,4-b)(1,5)diazepine-1H,4H-5,7-dione (a) 4-Benzene-azo-1-ethyl-5-(N-methyl-N-α-methoxycarbonylacetylamino)-3-methylpyrazole (1) 2.4 g (0.1 mole) of NaH are added to a solution of 14.5 g (0.1 mole) of methoxycarbonyl-N-methylacetamide (for the preparation, see H. Ulrich et al., J. Org. Chem. 27, 2160–2162) in 100 ml of dry dimethylformamide at room temperature, under a nitrogen atmosphere, and the mixture is subsequently stirred for 30 minutes. A solution of 24.8 g (0.1 mole) of 4-benzene-azo-5-chloro-3-methyl-1-ethylpyrazole in 50 ml of dimethylformamide is then slowly added dropwise, whilst cooling, and the mixture is warmed to 50° C. for one hour. 10 ml of ethanol and 5 ml of glacial acetic acid are added and the solution is evaporated in vacuo. The residue is taken up in $CHCl_3$ and the mixture is washed with water, dried with $Na_2SO_4$ and evaporated. Recrystallization of the residue from petroleum ether gives yellow-orange colored crystals of melting point 52°-53° C.

(2) 125 g (0.5 mole) of 4-benzene-azo-1-ethyl-3-methyl-5-methylaminopyrazole are reacted with 61 ml (0.55 mole) of monomethyl malonate chloride in 250 ml of benzene until the evolution of HCl has ended. The benzene is then stripped off in vacuo, the residue is taken up in CHCl₃ and the mixture is washed with cold NaHCO₃ solution and water, dried and evaporated. Recrystallization of the residue from petroleum ether gives crystals which are identical to the crystals described under 2 (a) (1).

(b)

4-Amino-1-ethyl-3-methyl-5-(N-methyl-N-α-methoxycarbonylacetylamino)-pyrazole 3.4 g (0.01 mole) of 4-benzene-azo-1-ethyl-5-(N-methyl-N-α-methoxycarbonylacetylamino)-3-methyl-pyrazole, dissolved in 100 ml of ethanol, are hydrogenated with 10 g of Raney nickel at 60° C. and under a hydrogen pressure of 50 atmospheres. When the uptake of hydrogen has ended, the catalyst is filtered off and the reaction solution is evaporated in vacuo. A colorless oil which cannot be crystallized remains as the residue.

(c)

1-Ethyl-3,8-dimethyl-5,6,7,8-tetrahydropyrazolo(3,4-b)(1,5)diazepine-1H,4H-5,7-dione The above oil is dissolved in ethanol and, after adding 1 ml of concentrated HCl, the mixture is boiled under reflux until the starting material has disappeared. The solution is then neutralized with alcoholic KOH solution and evaporated in vacuo, the residue is taken up in CHCl₃ and the mixture is dried and evaporated. The oil which remains crystallizes on trituration with ether. Melting point: 160° C.

(d)

1-Ethyl-3,8-dimethyl-4-phenyl-5,6,7,8-tetrahydropyrazolo(3,4-b)(1,5)diazepine-1H,4H-5,7-dione The reaction of 1-ethyl-3,8-dimethyl-5,6,7,8-tetrahydropyrazolo(3,4-b)(1,5)diazepine-1H,4H-5,7-dione with bromobenzene, copper powder and potassium acetate is carried out by the method described under Example 1 (d). Recrystallization of the product from diisopropyl ether gives the analytically pure product. Melting point: 149° C.

EXAMPLE 3

1-Isopropyl-3,8-dimethyl-4-phenyl-5,6,7,8-tetrahydropyrazolo(3,4-b)(1,5)diazepine-1H,4H-5,7-dione (a)

1-Isopropyl-3,8-dimethyl-5,6,7,8-tetrahydropyrazolo(3,4-b)(1,5)diazepine-1H,4H-5,7-dione A solution of 672 mg (0.004 mole) of 4-amino-1-isopropyl-3-methyl-5-methylaminopyrazole is slowly added dropwise to a solution of 280 mg (0.04 mole) of carbon suboxide (for the preparation, see H. Staudinger, S. Bereza, Ber. 41, 4461 (1908)) in 70 ml of ether, whilst cooling with ice. The mixture is then stirred for a further hour at 0° C. and the precipitate is filtered off. It is recrystallized from diisopropyl ether. Melting point: 163° C.

(b)

1-Isopropyl-3,8-dimethyl-4-phenyl-5,6,7,8-tetrahydropyrazolo(3,4-b)(1,5)diazepine-1H,4H-5,7-dione 2.3 g (0.01 mole) of 1-isopropyl-3,8-dimethyl-5,6,7,8-tetrahydropyrazolo(3,4-b)(1,5)diazepine-1H,4H-5,7-dione, 1.5 g (0.015 mole) of potassium acetate, 2.6 g (0.016 mole) of bromobenzene, 1.8 g of copper powder and 130 ml of dimethylformamide are heated to 150° C. for 15 hours, whilst stirring. The mixture is then filtered hot and the solvent is stripped off from the filtrate in vacuo. The residue is taken up in CHCl₃ and the mixture is washed with half-concentrated ammonia solution and then with water and is dried and evaporated. The residue is recrystallized from diisopropyl ether. Melting point: 165° C.

EXAMPLE 4

1-Ethyl-3-methyl-4-phenyl-5,6,7,8-tetrahydropyrazolo-(3,4-b)(1,5)diazepine-1H,4-5,7-dione 500 mg of the 1-ethyl-8-benzyl-3-methyl-4-phenyl-5,6,7,8-tetrahydropyrazolo(3,4-b)(1,5)diazepine-1H,4H-5,7-dione, accessible in the manner described in Synthesis Example 2, are dissolved in 100 ml of ethanol and are hydrogenated for 100 hours with platinum oxide as the catalyst, at 100° C. and under a hydrogen pressure of 150 atmospheres. The catalyst is then filtered off, the solvent is evaporated off from the filtrate in vacuo and the residue is filtered through a short silica gel column using CHCl₃/ethanol (9:1) as the running agent. The end product is then obtained in an analytically pure form. Melting point: 172° C.

The following compounds were also prepared in accordance with the instructions described:

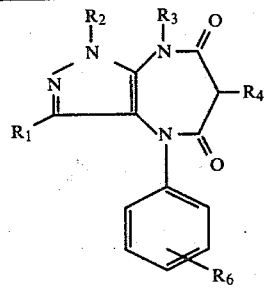

| Example | $R_1$ | $R_2$ | $R_3$ | $R_4$ | $R_6$ | Melting point (°C.) | Preparation method |
|---|---|---|---|---|---|---|---|
| 5 | —CH₃ | —CH₃ | —CH₃ | H | 3-Cl | 230 | 2 |

-continued

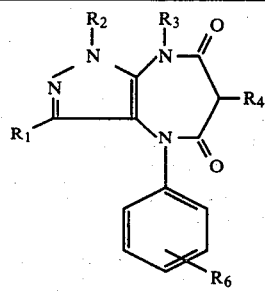

| Example | R₁ | R₂ | R₃ | R₄ | R₆ | Melting point (°C.) | Preparation method |
|---|---|---|---|---|---|---|---|
| 6 | —CH₃ | —CH₃ | —CH₃ | H | 2-Cl | 181 | 2 |
| 7 | —CH₃ | —CH₃ | —CH₃ | H | 4-CH₃ | 220 | 1 |
| 8 | —CH₃ | —CH₃ | —CH₃ | H | 4-F | 219 | 2 |
| 9 | —CH₃ | —CH₃ | —CH₃ | H | 4-Cl | 246 | 2 |
| 10 | —CH₃ | —CH₃ | —CH₃ | H | 3-F | 207–208 | 2 |
| 11 | —CH₃ | —C₂H₅ | —CH₃ | H | 2-Cl | 163 | 2 |
| 12 | —CH₃ | —C₂H₅ | —CH₃ | H | 4-F | 155 | 2 |
| 13 | —CH₃ | —C₂H₅ | —CH₃ | H | 4-Cl | 153 | 2 |
| 14 | —CH₃ | —C₂H₅ | —CH₃ | H | 4-CH₃ | 156 | 2 |
| 15 | —CH₃ | —C₂H₅ | —CH₃ | H | 3-Cl | 194 | 2 |
| 16 | —CH₃ | —C₂H₅ | —CH₃ | H | 3-CH₃ | 194 | 2 |
| 17 | CH₃ | C₂H₅ | CH₃ | H | 3-F | 167 | 2 |
| 18 | CH₃ | i-C₃H₇ | CH₃ | H | 2-Cl | 229 | 2 |
| 19 | CH₃ | i-C₃H₇ | CH₃ | H | 2-CH₃ | 154 | 2 |
| 20 | CH₃ | i-C₃H₇ | CH₃ | H | 4-F | 198 | 2 |
| 21 | CH₃ | i-C₃H₇ | CH₃ | H | 3-Cl | 160 | 2 |
| 22 | CH₃ | i-C₃H₇ | CH₃ | H | 4-Cl | 196 | 2 |
| 23 | CH₃ | i-C₃H₇ | CH₃ | H | 2-F | 182 | 2 |
| 24 | CH₃ | i-C₃H₇ | —CH₂—CH₂—OCH₃ | H | H | 136 | 2 |
| 25 | CH₃ | i-C₃H₇ | CH₃ | H | 3-F | 155 | 2 |
| 26 | CH₃ | CH₃ | CH₃ | H | 2-F | 181 | 2 |
| 27 | CH₃ | C₂H₅ | CH₃ | H | 2-F | 117 | 2 |
| 28 | C₂H₅ | CH₃ | CH₃ | H | H | 181 | 2 |
| 29 | —⟨S⟩ | CH₃ | CH₃ | H | H | 223 | 2 |
| 30 | —⟨S⟩ | C₂H₅ | CH₃ | H | H | 163 | 2 |
| 31 | CH₃ | H | CH₃ | H | H | 262 | 2 |
| 32 | n-C₃H₇ | C₂H₅ | CH₃ | H | H | 129 | 2 |
| 33 | n-C₃H₇ | CH₃ | CH₃ | H | H | 142 | 2 |
| 34 | CH₃ | —CH₂—Ph | CH₃ | H | H | 158 | 2 |
| 35 | CH₃ | CH₃ | —CH₂—Ph | H | H | 134 | 2 |
| 36 | H | CH₃ | CH₃ | H | H | 145 | 2 |
| 37 | CH₃ | CH₃ | H | H | H | 211 | 4 |
| 38 | CH₃ | CH₃ | C₂H₅ | H | H | 191 | 2 |
| 39 | CH₃ | CH₃ | n-C₃H₇ | H | H | 188 | 2 |
| 40 | CH₃ | CH₃ | ▷ (cyclopropyl) | H | H | 172 | 2 |
| 41 | CH₃ | CH₃ | —CH₂—CH₂—N(C₂H₅)₂ | H | H | 121 | 2 |
| 42 | CH₃ | CH₃ | —CH₂CF₃ | H | H | 234 | 2 |
| 43 | CH₃ | CH₃ | —CH₂—C≡CH | H | H | 177 | 2 |
| 44 | CF₃ | CH₃ | CH₃ | H | H | 163 | 2 |

What is claimed is:
1. A compound of the formula

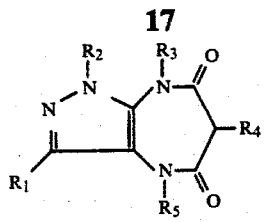

in which $R_1$ and $R_2$ are identical or different and represent hydrogen atoms or alkyl groups with 1-6 C atoms, it also being possible for one of the radicals $R_1$ and $R_2$ to be, in each case, a benzyl, trifluoromethyl or phenyl group, $R_3$ denotes a hydrogen atom, an alkyl group which has 1-6 C atoms and is optionally substituted by a phenyl group, an alkoxy group with 1-6 C atoms, a trifluoromethyl group, a dialkylamino groups with 2-12 C atoms or a cycloalkyl group with 3-6 C atoms, an alkenyl or alkynyl group with 2-6 C atoms, a cycloalkyl group with 3-6 C atoms or a carbalkoxy group with 2-6 atoms, $R_4$ is a hydrogen atom and $R_5$ can be a phenyl group, a phenyl group which is monosubstituted or disubstituted by methyl Cl, Br, F, nitro, cyano and or trifluoromethyl or a pyridyl group.

2. Compound according to claim 1, in which $R_1$ is $CH_3$, $R_2$ is hydrogen, $CH_3$, $C_2H_5$, $i$-$C_3H_7$ or phenyl, $R_3$ is $CH_3$, $R_4$ is hydrogen and $R_5$ is phenyl, monosubstituted or disubstituted phenyl or pyridyl.

3. Compound of the formula V

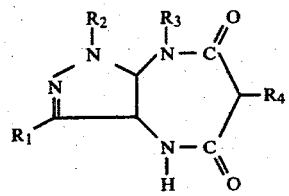

in which $R_1$, $R_2$, $R_3$ and $R_4$ are as defined in claim 1.

4. An anxiolytic composition containing as an active ingredient at least one compound according to claim 1 in an amount of from 1 to 50 mg, preferably 5 to 25 mg/dose, in admixture with the usual pharmaceutical excipients and auxiliaries.

* * * * *